US00PP21660P2

(12) United States Plant Patent
Sakazaki

(10) Patent No.: US PP21,660 P2
(45) Date of Patent: Jan. 18, 2011

(54) *CALIBRACHOA* PLANT NAMED 'USCAL53002'

(50) Latin Name: ***Calibrachoa* sp.**
Varietal Denomination: USCAL53002

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 12/590,819

(22) Filed: Nov. 14, 2009

(51) Int. Cl.
*A01H 5/00* (2006.01)

(52) U.S. Cl. ..... Plt./413

(58) Field of Classification Search ..... Plt./413
See application file for complete search history.

*Primary Examiner*—Kent L Bell
(74) *Attorney, Agent, or Firm*—C. A. Whealy

(57) ABSTRACT

A new and distinct cultivar of *Calibrachoa* plant named 'USCAL53002', characterized by its compact, mounding and outwardly spreading plant habit; vigorous and freely branching growth habit; dense and bushy appearance; freely flowering habit; small dark yellow-colored flowers; and good garden and summer performance.

1 Drawing Sheet

Botanical designation: *Calibrachoa* sp.
Cultivar denomination: 'USCAL53002'.

BACKGROUND OF THE INVENTION

The present invention relates to a new and distinct cultivar of *Calibrachoa* plant, botanically known as *Calibrachoa* sp. and hereinafter referred to by the name 'USCAL53002'.

The new *Calibrachoa* plant is a product of a planned breeding program conducted by the Inventor in Higashiomi, Shiga, Japan and Bonsall, Calif. The objective of the breeding program is to create new *Calibrachoa* plants with uniform plant habit, freely branching growth habit, attractive small flowers and good summer performance.

The new *Calibrachoa* plant originated from a cross-pollination made by the Inventor on May 5, 2006 in Higashiomi, Shiga, Japan of a proprietary seedling selection of *Calibrachoa* sp. identified as code number C423-01, not patented, as the female, or seed, parent with a proprietary seedling selection of *Calibrachoa* sp. identified as code number C445-02, not patented, as the male, or pollen, parent. The new *Calibrachoa* plant was discovered and selected by the Inventor as a single flowering plant within the progeny of the stated cross-pollination in a controlled environment in Bonsall, Calif. on Jul. 17, 2007.

Asexual reproduction of the new *Calibrachoa* plant by terminal cuttings in a controlled environment in Bonsall, Calif. since Jul. 20, 2007 has shown that the unique features of this new *Calibrachoa* plant are stable and reproduced true to type in successive generations.

SUMMARY OF THE INVENTION

Plants of the new *Calibrachoa* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'USCAL53002'. These characteristics in combination distinguish 'USCAL53002' as a new and distinct cultivar of *Calibrachoa:*

1. Compact, mounding and outwardly spreading plant habit.
2. Vigorous and freely branching growth habit; dense and bushy appearance.
3. Freely flowering habit.
4. Small dark yellow-colored flowers.
5. Good garden and summer performance.

The new *Calibrachoa* plant can be compared to plants of the female parent selection. Plants of the new *Calibrachoa* differ from plants of the female parent selection in the following characteristics:

1. Plants of the new *Calibrachoa* flower earlier than plants of the female parent selection.
2. Plants of the new *Calibrachoa* have larger flowers than plants of the female parent selection.
3. Plants of the new *Calibrachoa* and the female parent selection differ in flower color as plants of the female parent selection have light yellow-colored flowers.

The new *Calibrachoa* plant can be compared to plants of the male parent selection. Plants of the new *Calibrachoa* differ from plants of the male parent selection in the following characteristics:

1. Plants of the new *Calibrachoa* are more freely branching than plants of the male parent selection.
2. Plants of the new *Calibrachoa* have smaller flowers than plants of the male parent selection.

Plants of the new *Calibrachoa* can be compared to plants of the *Calibrachoa* 'USCALI402-1', disclosed in U.S. Plant Pat. No. 19,480. In side-by-side comparisons conducted in Bonsall, Calif., plants of the new *Calibrachoa* differed from plants of 'USCALI402-1' in the following characteristics:

1. Plants of the new *Calibrachoa* had more rounded flowers than plants of 'USCALI402-1'.
2. Plants of the new *Calibrachoa* had darker yellow-colored flowers than plants of 'USCALI402-1'.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the bottom of the sheet comprises a side perspective view of a typical flowering plant of 'USCAL53002' grown in a container.

The photograph at the top of the sheet comprises a close-up of typical flowers and leaves of 'USCAL53002'.

DETAILED BOTANICAL DESCRIPTION

The aforementioned photographs and following observations, measurements and values describe plants grown in 15-cm containers in Bonsall, Calif., under commercial practice during the summer and early autumn in an outdoor nursery with day temperatures ranging from 18° C. to 38° C. and night temperatures ranging from 9° C. to 18° C. Plants were pinched one time and were three months old when the photographs and description were taken. In the following description, color references are made to The Royal Horticultural Society Colour Chart, 2007 Edition, except where general terms of ordinary dictionary significance are used.

Botanical classification: *Calibrachoa* sp. 'USCAL53002'.

Parentage:

*Female, or seed, parent.*—Proprietary seedling selection of *Calibrachoa* sp. identified as code number C423-01, not patented.

*Male, or pollen, parent.*—Proprietary seedling selection of *Calibrachoa* sp. identified as code number C445-02, not patented.

Propagation:

*Type.*—By terminal cuttings.

*Time to produce a rooted young plant, summer.*—About 22 days at air temperatures of 29° C. and soil temperatures of 17° C.

*Time to produce a rooted young plant, winter.*—About 25 days at air temperatures of 21° C. and soil temperatures of 17° C.

*Root description.*—Medium in thickness, fibrous; white in color.

*Rooting habit.*—Freely branching; moderately dense.

Plant description:

*Plant and growth habit.*—Compact, mounding and outwardly spreading plant habit; freely branching habit with about ten primary lateral branches each with multiple secondary lateral branches; pinching enhances branching; vigorous, dense and bushy growth habit.

*Plant height.*—About 14 cm.

*Plant diameter.*—About 54 cm.

Lateral branch description:

*Length.*—About 28 cm.

*Diameter.*—About 3 mm.

*Internode length.*—About 2.5 cm.

*Strength.*—Strong.

*Aspect.*—Initially upright to outwardly spreading.

*Texture.*—Pubescent.

*Color.*—Close to 146B.

Foliage description:

*Arrangement.*—Before flowering, alternate, simple; after flowering, opposite, simple.

*Length.*—About 2 cm.

*Width.*—About 8 mm.

*Shape.*—Elliptical.

*Apex.*—Broadly acute to rounded.

*Base.*—Attenuate.

*Margin.*—Entire.

*Texture, upper and lower surfaces.*—Pubescent.

*Venation pattern.*—Pinnate; arcuate.

*Color.*—Developing leaves, upper surface: Close to 137B. Developing leaves, lower surface: Close to 137C. Fully expanded leaves, upper surface: Close to N137B; venation, close to 137C. Fully expanded leaves, lower surface: Close to 137C; venation, close to 146C.

*Petiole.*—Length: About 3 mm. Diameter: About 2 mm. Texture, upper and lower surfaces: Pubescent. Color, upper and lower surfaces: Close to 146D.

Flower description:

*Flower arrangement and habit.*—Single salverform flowers arising from leaf axils; freely flowering habit with usually about 22 to 36 open flowers and flower buds per lateral branch; flowers face upright and outwardly.

*Fragrance.*—None detected.

*Natural flowering season.*—Relatively early flowering habit, plants of the new *Calibrachoa* begin flowering about seven weeks after planting; plants flower continuously from spring though the autumn in Southern California.

*Flower longevity.*—Individual flowers last about five to seven days on the plant; flowers persistent.

*Flower diameter.*—About 3.2 cm.

*Flower length (height).*—About 2.4 cm.

*Flower throat diameter.*—About 5 mm by 8 mm.

*Flower tube diameter, base.*—About 2 mm.

*Flower tube length.*—About 1.9 cm.

*Flower bud.*—Shape: Elongated oblong. Length: About 2.3 cm. Diameter: About 5 mm. Color: Close to 150C to 150D.

*Corolla.*—Arrangement: Five petals fused at the base and opening into a flared trumpet. Petal lobe length (from throat): About 1.3 cm. Petal lobe width: About 1.6 cm. Petal shape: Roughly obdeltoid. Petal apex: Rounded. Petal margin: Entire. Petal texture, upper and lower surfaces: Smooth, glabrous. Throat texture: Smooth, glabrous. Tube texture: Pubescent. Color: Petal lobe, when opening, upper surface: Close to 5B to 5C. Petal lobe, when opening, lower surface: Close to 5D. Petal lobe, fully opened, upper surface: Close to 13B; color becoming closer to 12C with development; towards the throat, close to 12A; venation, close to 145B. Petal lobe, fully opened, lower surface: Close to 5D; venation, close to 145C. Throat: Close to 13A; venation, close to 164C. Tube: Close to 12C; venation, close to 145C.

*Calyx.*—Arrangement: One star-shaped calyx tube with five sepals in a single whorl and fused at the base. Sepal length: About 1.6 cm. Sepal width: About 3 mm. Sepal shape: Lanceolate. Sepal apex: Acute. Sepal margin: Entire. Sepal texture, upper and lower surfaces: Pubescent. Color, upper and lower surfaces: Close to 146A.

*Peduncles.*—Length: About 2.6 cm. Diameter: About 1 mm. Angle: About 45° to 60° from stem axis. Strength: Moderately strong. Texture: Pubescent. Color: Close to 144A.

*Reproductive organs.*—Stamens: Quantity/arrangement: About five per flower. Filament length: About 1.1 cm. Filament color: Close to 145D. Anther shape: Oval. Anther length: About 1.5 mm. Anther color: Close to 8C. Pollen amount: Moderate. Pollen color: Close to 8B. Pistils: Quantity: One per flower. Pistil length: About 1.2 cm.

*Seed/fruit.*—Seed and fruit development have not been observed on plants of the new *Calibrachoa.*

Garden performance: Plants of the new *Calibrachoa* have been observed to have good garden performance and tolerate wind, rain and temperatures ranging from 1° C. to about 40° C.

Pathogen/pest resistance: Plants of the new *Calibrachoa* have not been observed to be resistant to pathogens and pests common to *Calibrachoa.*

It is claimed:

1. A new and distinct *Calibrachoa* plant named 'USCAL53002' as illustrated and described.

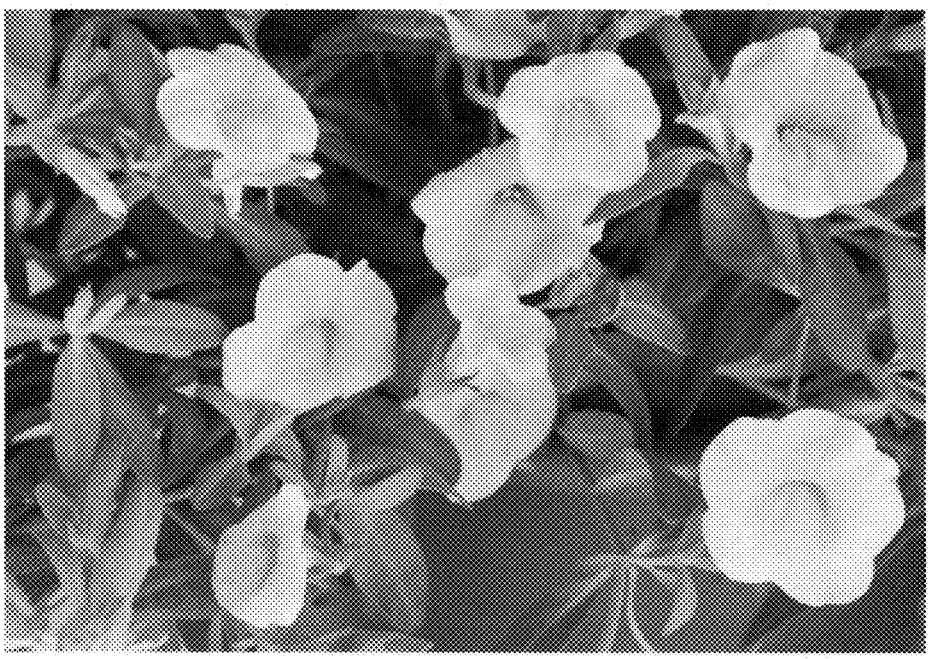
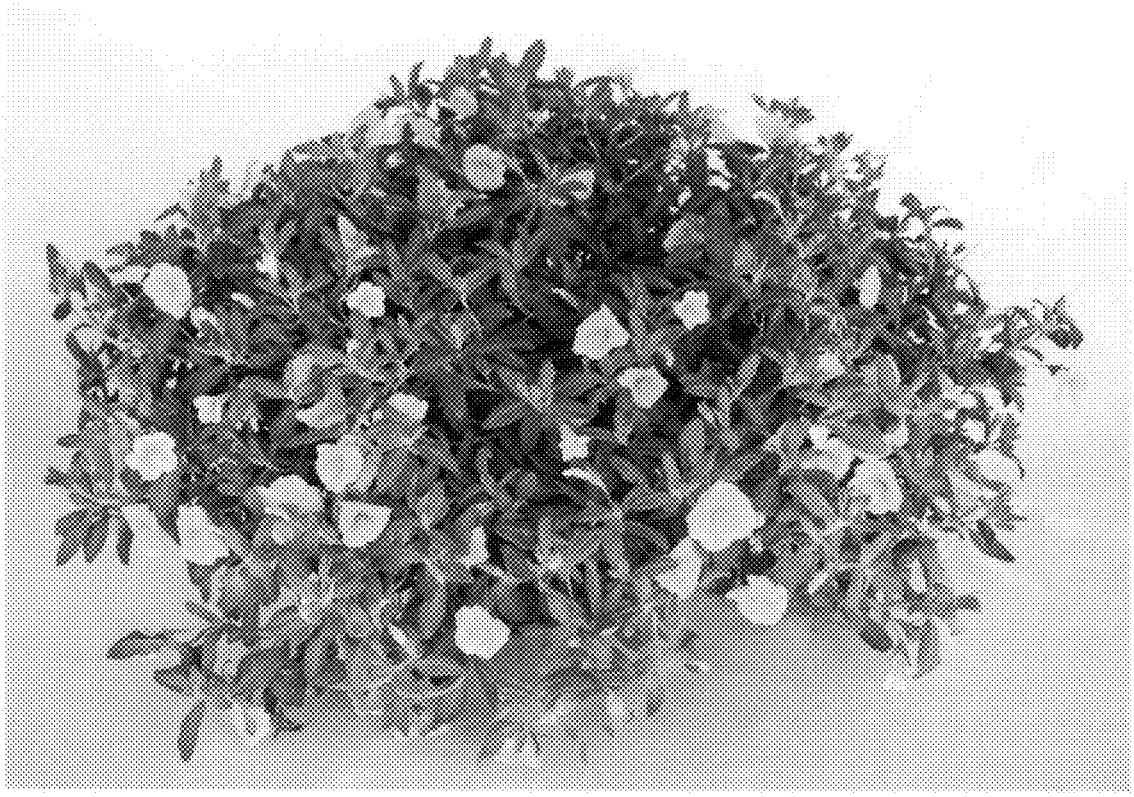

* * * * *